United States Patent [19]

Bowen

[11] 4,425,916

[45] Jan. 17, 1984

[54] CAP STRUCTURE FOR CREATING TEMPERATURE CONTROLLED ENVIRONMENT FOR REDUCING ALOPECIA

[75] Inventor: Mark Bowen, Los Angeles, Calif.

[73] Assignee: Therapeutic Products, Inc., Los Angeles, Calif.

[21] Appl. No.: 44,510

[22] Filed: Jun. 1, 1979

[51] Int. Cl.³ ............................................. A61F 7/00
[52] U.S. Cl. .................................... 128/403; 128/402
[58] Field of Search ............... 128/399, 402, 403, 327, 128/380, 379

[56] References Cited

U.S. PATENT DOCUMENTS

| | | | |
|---|---|---|---|
| 2,519,712 | 8/1950 | Stegeman | 128/327 |
| 3,059,645 | 10/1962 | Hasbrouck et al. | 128/327 |
| 3,463,161 | 8/1969 | Andrassy | 128/402 |
| 3,491,761 | 1/1970 | Baker | 128/402 |
| 3,506,013 | 4/1970 | Zdenek | 128/402 |
| 3,696,814 | 10/1972 | Umemoto | 128/402 |
| 4,172,495 | 10/1979 | Zebuhr et al. | 128/402 |
| 4,190,054 | 2/1980 | Brennan | 128/402 |
| 4,204,543 | 5/1980 | Henderson | 128/403 |

OTHER PUBLICATIONS

Prevention of Doxorubicin-Induced Hair Loss With Scalp Hypothermia", J. C. Dean et al., New England, J. of Medicine, Dec. 27, 1979, vol. 301, #26, pp. 1427-1429.

Primary Examiner—C. Fred Rosenbaum
Assistant Examiner—C. W. Shedd
Attorney, Agent, or Firm—Freilich, Hornbaker, Rosen & Fernandez

[57] ABSTRACT

A cap structure for application to the head of a patient to create a cold environment around the scalp portion of the patient during cytotoxic treatment, thereby to reduce alopecia which might arise as a result of the treatment. The cap structure is comprised of a plurality of individual cap structure forming sections or panels with each panel having at least one internal chamber. A substance in each of these internal chambers is capable of being subjected to and achieving a reduced temperature, and of retaining a reduced temperature for a substantial period of time. The cap sections are connected together by flexible members in order to facilitate conforming the cap structure to the patient. The cap structure may include an upper section, two side sections and a rear section, which sections may be fastened together for use, and unfastened for cleaning and/or storage. The cap structure could also be comprised of a unitary member which may be provided with a plurality of panels separated by flexible members.

1 Claim, 10 Drawing Figures

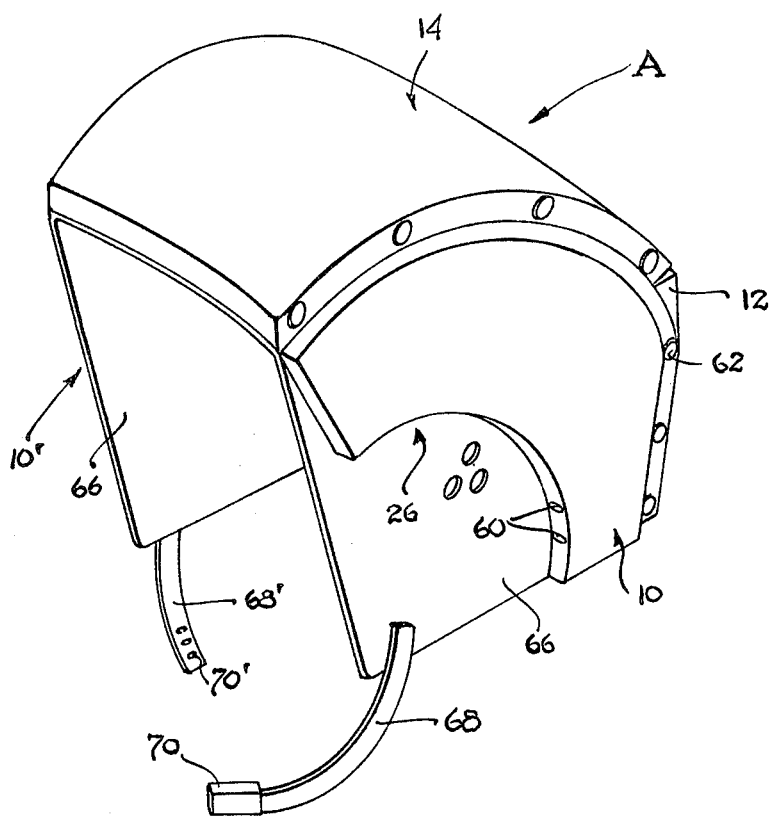
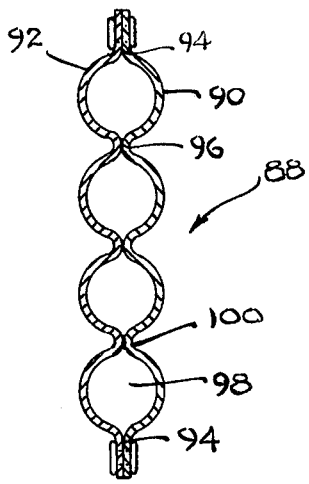
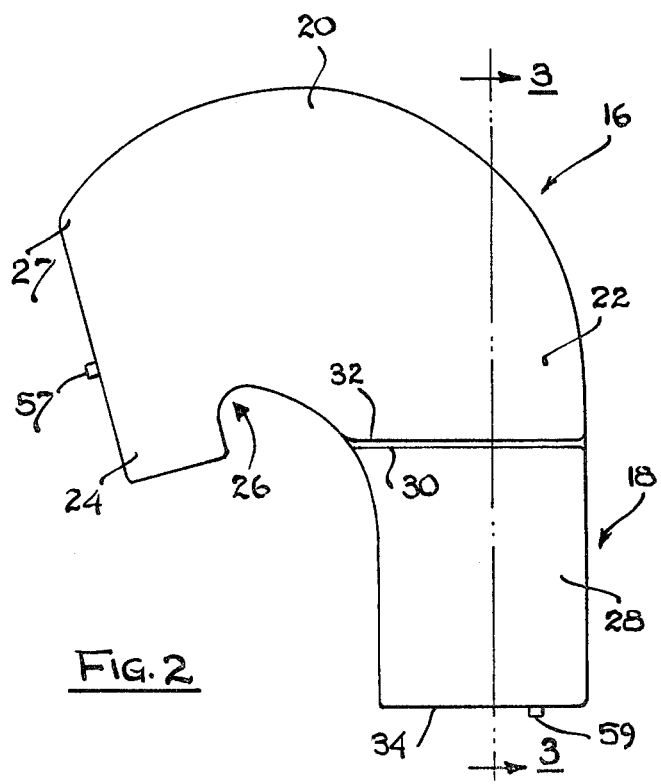
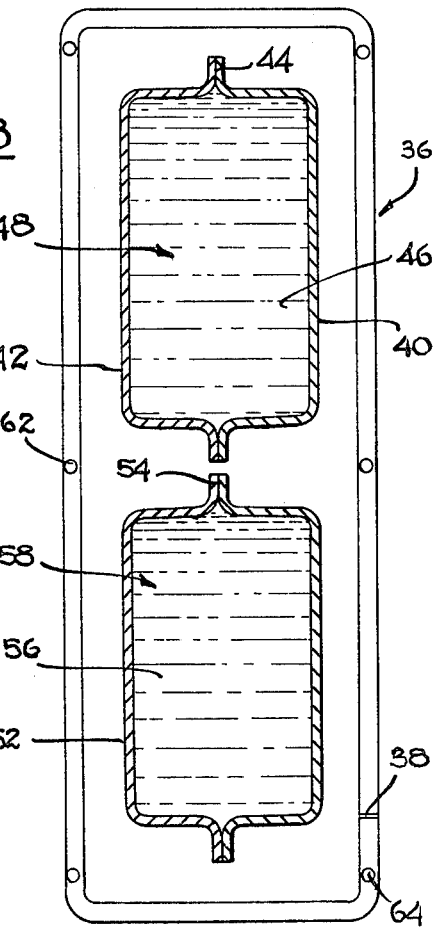

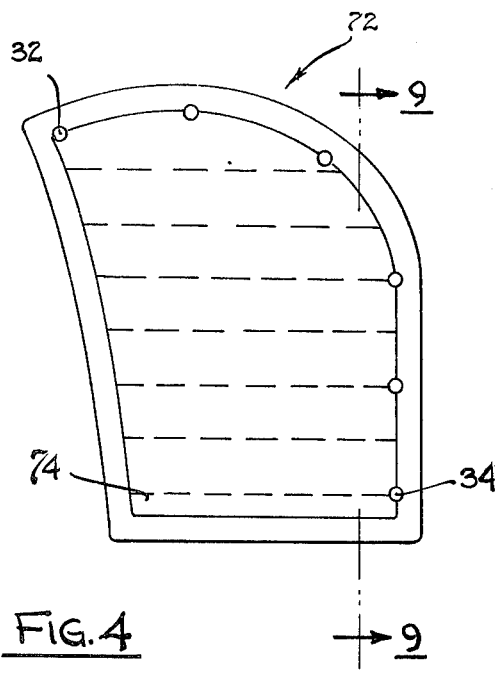
FIG.4
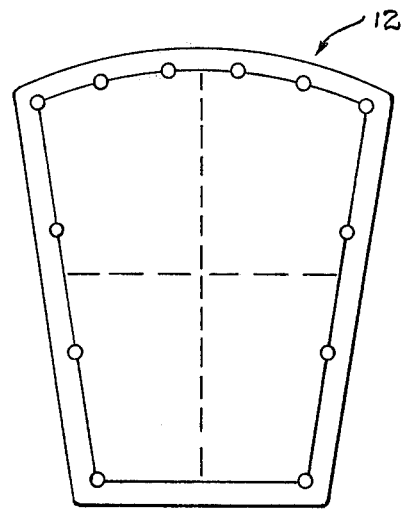
FIG.5
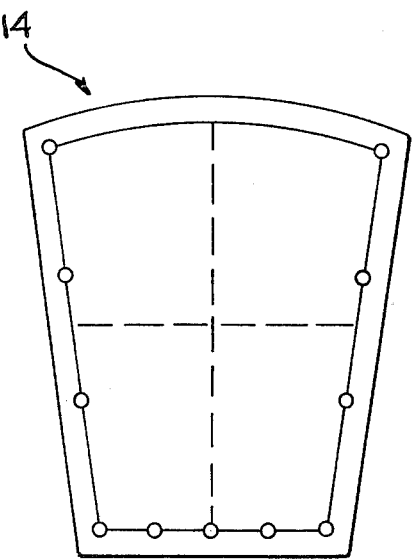
FIG.6
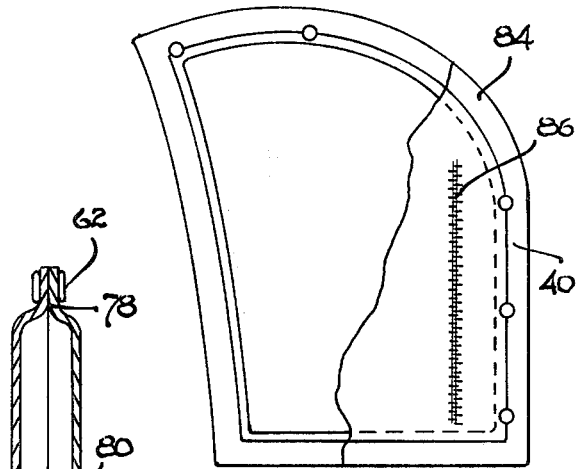
FIG.7
FIG.8
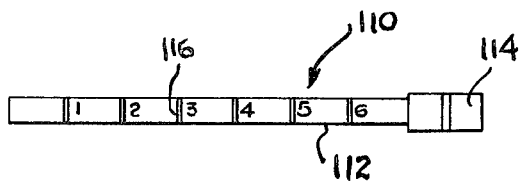
FIG.10

CAP STRUCTURE FOR CREATING TEMPERATURE CONTROLLED ENVIRONMENT FOR REDUCING ALOPECIA

BACKGROUND OF THE INVENTION

1. Field of the Invention

This invention relates in general to certain new and useful improvements in cap structures for maintaining reduced temperature environments around the scalp portion of the wearer, and more particularly, to cap structures which are capable of being conformed to heads of particular wearers, and also to improved methods of reducing alopecia.

2. Brief Description of the Prior Art

It is well known that certain chemotherapeutic agents can be introduced into individuals suffering from cytotoxic cancer, and include, for example, such agents as adriamycin and other agents offered under the tradename "Cytoxan", which is a cyclophosphomide, etc. These cytotoxic agents oftentimes produce various undesirable side effects. These agents, and particularly adriamycin, while effective in arresting certain carcinomas, usually cause a loss of hair to a substantial degree.

It is also well known that in an effort to reduce the effect of hair loss, blood circulation to the scalp can be reduced. In many cases, chemotherapists have attempted to apply ice packs to the scalp portion of the individual receiving the cytotoxic drug. However, in an attempt to reduce hair loss, typically referred to as alopecia, it is necessary to apply a cold environment to the scalp for a substantial period of time in temporal relation to the introduction of the cytotoxic agent. Consequently, a physician's aide or nurse must be present in order to help the patient with the retention of the ice packs on the scalp portion of the patient.

Oftentimes, the patient who is to receive the cytotoxic agent is aware of the harmful side effects and may be in a somewhat despondent state. In such a condition, the patient is oftentimes not capable of retaining the ice pack on his or her head. After the injection of the cytotoxic agent, the patient may also be suffering from other side effects, and, therefore, also is not capable of being relied upon to hold the ice packs or similar cold media on the scalp portion.

There has been a need for some effective, but yet relatively inexpensive mechanism for maintaining a cold environment around the scalp portion of a party receiving a chemotherapeutic agent, and which does not require a substantial amount of manual assistance.

OBJECTS OF THE INVENTION

It is, therefore, a primary object of the present invention to provide a cap structure which is formed of a plurality of chambers having a substance capable of retaining a relatively low temperature for a substantial period of time so as to create a reduced temperature environment around the scalp portion of a wearer for a substantial period of time.

It is another object of the present invention to provide a cap structure of the type stated which contains a substance which when subjected to reduced temperatures, is capable of retaining a relatively low temperature for substantial periods of time.

It is also an object of the present invention to provide a cap structure of the type stated which may contain a frozen liquid in the chambers thereof but which is nevertheless flexible so as to conform to the head of the user when the somewhat liquid substance has been hardened.

It is still another object of the present invention to provide a cap structure of the type stated which is comprised of a plurality of individual cap structure forming sections attached to each other by flexible members so as to conform to the size and shape of the wearer.

It is still a further object of the present invention to provide a cap structure of the type stated which can be formed of a minimum number of sections and yet capable of being fitted to a number of individuals having varying head sizes.

It is another salient object of the present invention to provide a cap structure of the type stated which substantially reduces the amount of time required by medical personnel to attend to the user.

It is an additional object of the present invention to provide a method for reducing alopecia by applying a cap structure to the scalp portion of the user for a period of time preceeding an injection of a chemotherapeutic agent and for a period of time after receiving the injection of a chemotherapeutic agent.

It is yet another salient object of the present invention to provide a method of the type stated which is highly effective in reducing alopecia as a result of the application of chemotherapeutic agents and which also substantially reduces the amount of assistance required by medical personnel to a recipient of a chemotherapeutic agent.

With the above and other objects in view, my invention resides in the novel features of form, construction, arrangement and combination of parts presently described and pointed out in the claims.

BRIEF SUMMARY OF THE DISCLOSURE

A cap structure for application to a human head and which is preferably designed to cover a substantial portion of the scalp of the wearer. In one embodiment of the invention, the cap structure is comprised of a plurality of individual cap structure forming sections or so-called "panels". These panels each contain at least one compartment of the type capable of receiving a substance which is generally liquid or somewhat liquid at room temperature and capable of being gelid when subjected to reduced temperatures, and which substance is also capable of holding a relatively low temperature for a substantial period of time. Thus, when the cap structure forming section is subjected to a relatively low temperature, the liquid substance will become gelid and thereby become relatively hard and not easily conformable to a head portion. However, the invention utilizes the individual sections which are attachable together so as to conform to the size and general overall shape of a particular human head.

In a more preferred aspect of the invention, a top panel or section, and two side panels or sections, and a rear panel or section is provided. Initially, these panels are attached and then disposed over a synthetic head form in order to provide a general conformance to a normal overall head size and shape, and thereafter placed in an environment of reduced temperature so that the liquid substance will freeze and become hardened. In the frozen state, the substance will retain its relatively low temperature for a substantial period of time.

It is also possible to provide each of the individual cap structure forming sections with a plurality of individual cap structure forming sections with a plurality of individual chambers having the liquid substance contained therein. These individual chambers are separated by flexible portions which enable the overall section to have some flexibility when being applied to the head of a user. In this way, the cap structure can easily conform to the head size and shape of the user. Moreover, by virtue of the fact that the liquid substance which is employed retains a low temperature for a substantial period of time, it is possible to reduce blood circulation around the scalp portion of the user and thereby potentially reduce alopecia.

In one embodiment of the invention, it is possible to construct each of the cap structure forming sections with a pair of plys of flexible materials, as for example, plys of flexible plastic materials. The pair of plys are normally cut to the proper size and shape of the section to be formed and sealed together along their periphery or in close proximity to the periphery of the plys of material. In addition, and in order to form the individual spaced-apart substance receiving chambers, the plys are also sealed at intermediate points between the seals along the periphery. Also, in a preferred embodiment, the individual cap structure forming sections are enclosed within outer linings.

The term relatively low temperature which is created by the cap structure is low relative to body temperature, as for example, about 0° C. The relatively low temperature could be below 0° C., e.g. −20° C., or otherwise above the temperature of 0° C.; although it should not be so low that it will cause frostbite or other adverse conditions on the head of the wearer when used for a reasonable period of time, e.g., one hour or so.

The liquid substance is one which does not necessarily have to freeze when subjected to a reduced temperature environment to achieve the relatively low temperature. It should, however, be capable of retaining a relatively low temperature for a substantial period of time, that is perhaps about one-half hour to about two hours, namely the amount of time that the user might wear the cap structure. It is desirable to use a liquid substance which is capable of being frozen to achieve the relatively low temperature so as to be capable of holding a relatively low temperature for a substantial period of time.

The liquid substance may be liquid at room temperature and yet is capable of being frozen to become hardened at temperatures somewhat below room temperature, as for example, water, which is liquid at room temperature and frozen at and below 0° C. The term liquid substances would also include various compositions which are more viscous than water at room temperature, as for example, certain gels which are now available for retaining a reduced temperature for a substantial period of time.

This invention possesses many other advantages and has other purposes which may be more clearly apparent from a consideration of the forms in which it may be embodied. These forms are shown in the drawings forming and accompanying part of the present specification. They will now be described in detail for the purposes of illustrating the general principles of the invention, but it is to be understood that such detailed descriptions are not to be taken in a limiting sense.

BRIEF DESCRIPTION OF THE DRAWINGS

Having thus described the invention in general terms, reference will now be made to the accompanying drawings in which:

FIG. 1 is a perspective view of a cap structure constructed in accordance with and embodying the present invention;

FIG. 2 is an elevational view of one side panel assembly forming part of the cap structure of the present invention;

FIG. 3 is a vertical sectional view taken along line 3-2 of FIG. 2;

FIG. 4 is an elevational view of another form of side panel forming part of the cap structure of the present invention;

FIG. 5 is an elevational view of a back panel forming part of the cap structure of the present invention;

FIG. 6 is a top plan view of a top panel forming part of the cap structure of the invention;

FIG. 7 is an elevational view, somewhat similar to FIG. 2, and showing the panel of FIG. 4 in a removable covering;

FIG. 8 is a vertical, sectional view taken along line 8—8 of FIG. 2;

FIG. 9 is a vertical sectional view, somewhat similar to FIG. 8, and showing a modified form of panel forming part of the cap structure of the present invention; and FIG. 10 is a side elevational view of a tourniquet which may be used in performing the method of the present invention.

DETAILED DESCRIPTION OF PRACTICAL EMBODIMENTS

Referring now in more detail and by reference characters to the drawings which illustrate practical embodiments of the present invention, A designates a cap structure generally comprised of a pair of side panel assemblies 10 and 10', a back panel or rear panel 12, and a top panel 14. These paanels are each often referred to as a "cap structure forming section" inasmuch as, in combination, they form the cap structure A.

Only one of the side panel assemblies 10 is more fully illustrated in FIGS. 2 and 3 inasmuch as the other of the side panel assemblies 10' is substantially similar in construction and operation.

The side panel assembly 10 is comprised of a pair of individual panel sections 16 and 18 often referred to as "packets" inasmuch as they constitute a packet containing a liquid substance hereinafter described. The upper packet or panel section 16 is comprised of a main body portion 20 adapted to extend along a major portion of the side of the wearer's head and an integrally formed rearwardly located, downwardly struck portion 22 which extends behind the ear of the wearer. In like manner, the main body portion 20 is provided with an integrally formed downwardly extending sideburn covering portion 24, which together with the main body portion 20 and the rearwardly located downwardly struck portion 22, form an arcuately shaped ear receiving recess 26. The main body portion 20 is further provided with an integrally formed slightly forwardly extending temple covering portion 27.

The panel forming section 18 is comprised of a somewhat vertically disposed main body section 28 having an upper margin 30 disposed in close proximity to a lower margin 32 on the downwardly struck portion 22 of the upper panel section 16. Moreover, the lower panel section 18 has a width at its upper end approximately equal to the width of the lower end of the downwardly struck portion 22. However, the overall dimension of the panel section 18, at its lower end 34, is increased somewhat in order to substantially fully cover all portions of the scalp about the lower side portion of the scalp of the wearer.

In the embodiment of the invention, as illustrated, the panel sections 16 and 18 are enclosed within an outer cover 36, the latter having an interior compartment 37 sized and shaped to receive the panel sections 16 and 18. Moreover, the cover 36 would be provided with an opening 38 in the form of a slit, as illustrated, and which may be openable and closeable to receive the panel sections 16 and 18. The opening 38 may be provided with a locking means, as for example, a zipper, or the like.

The outer cover may be provided for decorative purposes and also to hold the individual panel sections in a desired relation to one another, and for other purposes hereinafter described in more detail.

Each of the individual panel sections are comprised of a pair of plys of material, as for example, plys of plastic material. Thus, the upper panel section 16 is comprised of a pair of spaced-apart plys 40 and 42 which are sealed along their entire periphery by means of a peripherally extending heat seal 44. In this way, the plys form an interior substance receiving chamber 46 which has included therein a liquid substance 48. The lower panel section 18 is similarly comprised of a pair of spaced-apart plys 50 and 52 which are sealed along their entire periphery by means of a peripherally extending heat seal 54 to form an interior substance receiving chamber 56 having a similar liquid substance 58 therein.

Sealable openings 57 and 59 are provided on the sections 16 and 18, respectively, for introducing the liquid substance therein. These openings are sealed and preferably permanently sealed after the liquid substance has been so introduced. It should be understood that similar openings would be formed on each of the other panels and sections forming part of the cap structure of the present invention.

In addition, the outer covers, e.g., the cover 36, may be provided with one or more air inlet apertures 60 so as to permit air to enter the interior compartments of the covers, such as the compartment 37, of the outer cover 36. In this way, the air in the compartment will not become stale giving rise to growth of bacterial conditions or other undesirable conditions. One of such air inlet apertures 60 is illustrated in FIG. 1 of the drawings. The air inlet apertures 60 are preferably surrounded by grommets in order to prevent tearing of the material forming the outer covers.

The individual side panel assemblies 10 and 10' are adapted to be removably attached to the top panel 14 and the back panel 12 as aforesaid. For this purpose, the panels 12 and 14 and the panel assemblies 10 and 10' would be provided with releasable fastening means. When the panels are each included within an outer cover, as in the illustrated embodiment, then the outer covers would be provided with the releasable fastening means.

The cover 36 which holds the cap structure forming sections 10 and 10' is also provided at or in close proximity to its periphery with a fastening means. In the illustrated embodiment of the invention, the fastening means comprises a plurality of snap-fasteners 62 which are capable of mating with releasable cooperating snap-fasteners 64. Thus, each of the individual cap structure forming sections hereinafter described and the cap structure forming sections 10 and 10' may be provided with one of the type of snap-fasteners 62 or complements of both, e.g., fasteners 62 and 64, so as to be able to become releasably attached to the other of the cap structure forming sections, as hereinafter described.

The covers for the side panel sections 10 and 10' are each provided with a single ply or sheet 66 and 66', respectively, on each of the opposite sides thereof, constituting face covering portions, and particularly, cheek covering portions. Further, at their lower ends, the cheek covering portions 66 and 66' are provided with flexible straps 68 and 68'. The 68 and 68' straps may be provided with, at their lower ends, a releasable attaching means to enable the straps to be releasably secured under the neck of the wearer of the cap structure. One such releasable attaching means may comprise a buckle 70 on one strap and apertures 70' on the other to be received by the buckle. The attachment means could also be attachment fiber strips marketed under the brand name "Velcro". Otherwise, the releasable attaching means may adopt any other form of attaching mechanism. It is not absolutely necessary to provide an independent releasable attaching means in that the straps could be releasably attached by tying the same under the neck of the wearer. In this same respect, tie strings or other means for attaching the cap portion to the head of the wearer could be employed in place of the straps 68 and 68' as illustrated.

This construction is advantageous in that it substantially reduces airflow of ambient temperature air around the scalp of the wearer when the cap structure is donned. The side cheek covering plys snuggly engage the cheeks, and the cap is tightly secured to the user by virtue of the straps 68 and 68' in order to reduce ambient air flow into the interior of the cap structure. In this way, the relatively low temperature environment may be maintained around the scalp of the user for a substantial period of time.

FIGS. 4 and 8 of the drawings illustrate another form of side panel or side cap structure forming section 72 which may be used in the present invention. This panel 72 is somewhat similar to the panels 10 and 10' illustrated in FIGS. 1 and 2 of the drawings, except that the panel 70 is comprised of a single packet containing the liquid substance as opposed to two individual packets. Further, the shape of the side panel is slightly different.

The side panel 72 illustrated in FIGS. 4 and 8 is comprised of a pair of plys 74 and 76 of material, such as plastic material, which are heat sealed by means of a heat seal 78, along their entire periphery to form an interior liquid substance receiving chamber 80. Thus, the means for forming the side panel 70 is similar to the means for forming the individual side panel sections 10 and 10', and the operation is similar. In the embodiment of the side panel 70, as illustrated in FIGS. 4 and 8, the side panel is not included within an outer cover and, therefore, the releasable attaching means in the form of the snap fasteners 62 and 64 are secured to the plys 74 and 76 at or in close proximity to the periphery of these plys. In the illustrated embodiment, the snap fasteners 62 and 64 are located almost on the peripheral heat seal 78. In this way, the snap fasteners do not extend through the liquid substance receiving chamber and further, are located along a fairly strengthened portion of the two plys 74 and 76.

The fasteners such as the snap-fasteners are thereafter applied to the panels or otherwise the cover for the panels in accordance with conventionally known techniques. For example, the so-called "fastener guns" may be employed to attach the corresponding halves of the snaps to the two plies (or covers) in the manner as illustrated. It should also be understood in connection with the present invention that the snaps are the preferred form of attaching the various sections; although other forms of releasably attaching the sections could be provided. For example, releasable fiber strips of the type sold under the brand name "Velcro" could be applied along the periphery of each of the individual cap forming sections (or covers for the sections, if employed). Otherwise, zippers or similar means of releasably attaching the sections could be provided.

In one of the embodiments of the invention, the various panels may be included in outer linings or covers, as indicated previously. For example, the panel 72, as illustrated in FIG. 4, is included within an outer lining or cover 84, as illustrated in FIG. 7. In this case, the outer cover 84 may be of a cloth type material or it also may be formed of a plastic type material. The outer cover is to protect the various panels from abuse, and, further, may also provide an aesthetic appearance to the various panels. In the event that an outer cover is employed, it is preferably removable for purposes of cleaning and changing. In addition, the outer cover, if employed, would be provided with the fastening means, as in the case with the outer cover 36. Thus, in the embodiment as illustrated in FIG. 7, the fastening means, as for example, the snap-fasteners, are secured to the outer lining as opposed to the panel itself. In the embodiment as illustrated, the outer cover 84 is conveniently provided on one of its side walls with a zipper 86 as illustrated.

In one of the embodiments of the invention, the various panels or cap structure forming sections may be comprised of a plurality of hermetically sealed individual chambers which are separated from one another and are designed to receive the liquid substance. One of such panels 88 is more fully illustrated in FIG. 9 of the drawings. In this case, and for purposes of illustration, the panel 88 of FIG. 9 is similar to the panel 72 illustrated in FIGS. 4 and 8. Thus, the cross-sectional configuration of the panel 88 of FIG. 9 is similar to the cross-sectional configuration of the panel of FIG. 8. FIG. 4 also illustrates in dotted lines a plurality of individual horizontally extending vertically spaced-apart chambers. These dotted lines would not exist in the arrangement of FIG. 8 but would be present in the arrangement of FIG. 9.

The panel 88 is comprised of a pair of plys 90 and 92 which are heat sealed together along their peripheries or in close proximity to their peripheries by peripherally extending heat seals or welds 94. In addition, the two plies 90 and 92 are sealed together at a plurality of spaced-apart locations thereby forming transversely extending seal lines 96 in the manner as illustrated in FIG. 9. These seal lines 90 form individual isolated liquid receiving compartments 98 within each of the panels or structure forming sections. It can be observed that each of the vertically spaced-apart individual chambers 98 extend essentially for the entire width of the transverse dimension of the panel 98, at least from one portion of the peripheral seal 94 to the other opposite portion of the peripheral seal 94. Moreover, each of the individual chambers 98 are connected by portions of the plies 90 and 92 which, in turn, constitute webs 100, and which are generally flexible, even when a liquid composition in in the chambers 98 is hardened.

It should also be understood that the various individual liquid receiving chambers 98 could be separated from each other by a greater distance. However, they should not be separated by any substantial distance, or otherwise, an uneven cooling environment would be created across the scalp portion of the user. In addition, while this construction having a plurality of individual liquid substance receiving chambers has been shown in connection with one of the side panels, it could be included in the top and back panels as well. If used in the top panel, the various intermediate welds and, hence, the intermediate chambers would extend longitudinally so as to extend between the front and rear portions of the wearer's head. In the back panels, the welds and, hence, the chambers would extend horizontally.

Each of the remaining panels or sections 12 and 14 are similar in construction and may adopt any of the foregoing embodiments. Thus, for example, the rear panel can be provided with transversely extending individual spaced-apart liquid substance chambers, and the top panel could be provided with longitudinally extending and transversely spaced-apart liquid substance receiving chambers. Further, all panels could be included in outer covers. Otherwise, the construction of these components are similar to the construction of the side panels.

The side panels 72 are each somewhat rectangular in shape although the forward margins are somewhat arcuately shaped. At their upper ends, the forward margins protrude slightly forwardly so as to cover the temple portion of the scalp of the wearer. If desired, recesses could be formed in the side panels so as to extend around the ears as in the embodiments of the side panels 10 and 10' and thereby avoid the inclusion of the ears in the reduced temperature environment.

The top panel 14 is somewhat trapezoidal in shape although the corners are slightly rounded. In addition, the back panel 12 is somewhat trapezoidal in shape, although the upper margin thereof is provided with an arcuate shape so as to conform to the arcuate shape of the crown portion of the wearer's head.

In the embodiment of the invention as illustrated, the back panel is comprised of four individual panel sections, as shown, which would include 12a, 12b, 12c and 12d in allotted arrangement. In like manner, the top panel 14 is comprised of four sections 14a, 14b, 14c and 14d in the illustrated arrangement. Further, in these illustrated embodiments, the various panel sections are actually included in a cover having a peripheral seal and with snap-fasteners on the cover. However, as indicated above, the top and back panels could each be formed with a single panel having a plurality of separate chambers.

The various panels, and particularly, the plys, e.g., the plys 40 and 42, and plys 50 and 52, plys 74 and 76, etc., may be formed of a number of known plastic materials, as for example, polyethylene, polystyrene, various vinyl compounds, and the like. Moreover, these plys used in the construction of the panels may be die-cut and heat sealed to each other by conventional radio frequency heating equipment. Moreover, the panels could be formed in various molding operation such as a number of known plastic molding operations.

It should also be understood that the plys could be formed of cloth or preferably plastic impregnated cloth materials. Further, the panels need not be formed of a pair of plys but could be formed of a single piece of plastic or cloth sealed in another manner to construct the panels as shown and described herein. In any case, the materials used must be designed so that there is easy heat transfer, e.g., to permit the cold environment to be established around the user's head. The same holds true in constructing the covers for the various panels.

In one of the more preferred embodiments, the various plies are formed of a vinyl impregnated nylon type material which is highly durable and will not crack when subjected to substantial temperature changes. In the same respect, the other plastics, if used, should be impregnated with suitable components in order to prevent cracking or deterioration due to the constant subjection to various temperature environments.

In one of the preferred embodiments of the invention, the side panels may always be of the same size and shape. Three different sizes of back panels and three different sizes of top panels would be employed. In this way, it has been found, in connection with the present invention, that it is only necessary to change the top and back panels in order to accommodate various head sizes with the size panels basically remaining of the same size and shape. In addition, it is found that three different sized top panels and three different sized back panels could be used with a large sized back panel and a top panel fitting a large head, a medium sized back panel and top panel fitting a medium head size, and a small sized back panel and top panel fitting a small head size, as for example, a child's head.

In accordance with the above outlined construction, when the cap structure is donned by a user, it essentially covers, in close fitting engagement, the scalp portion of the wearer. It is not necessary to actually have the cap in physical contact, but only to create a temperature controlled environment around the scalp portion in order to reduce the temperature of the scalp portion. Inasmuch as the liquid substance which is contained within the chambers of the various panels is capable of retaining a low temperature for a substantial period of time, the user can wear the cap without a great deal of discomfort and still maintain a substantially reduced temperature around the entire scalp portion both prior to and after an injection of a cytotoxic drug.

For the purpose of achieving close fitting engagement, a pair of straps extending from opposite sides of the cap structure and adapted to extend over the forehead of the wearer could be provided. These straps could also be tie straps, or otherwise, could be provided with fastening means of the type described above.

Any form of liquid may be employed in connection with the present invention although it should meet the criteria established above. In other words, preferably, it should be capable of being frozen when subjected to relatively low temperature, e.g., reasonably within the range of the freezing point of water. One of the preferred forms of liquid substance is a gel refrigerant and, preferably, a gel refrigerant comprised of starch and borax, of the type described in U.S. Pat. No. 2,800,454 and U.S. Pat. No. 2,800,455. Other forms of so-called "slow melting ices" of the type described in U.S. Pat. No. 2,490,047 could also be employed. While the gel does not change from a true liquid form to a solid form, and more specifically, changes from a semi-solid form to a solid form, on freezing, it will nevertheless be considered a "liquid substance" in connection with the present invention since it has some slight degree of free-flowing capability when not frozen.

In using the cap structure of the invention, and performing the method for reducing alopecia, an attendant to the user, as for example, a physician's aide, will first assemble the proper sections of the cap structure for the approximate head size of the user. Thereafter, these sections will be removably attached together, as for example, by means of the snap fasteners. While the liquid substance is still in a liquid stage, the assembled sections which constitute the cap structure will then be placed on an articial head form in order to approximate the size and shape of an individual's head. In this respect, three different head forms could be provided, namely, a "large", "intermediate" and "small" head forms. Thereafter, the head form with the cap structure thereon is placed in an environment of reduced temperature, as for example, a refrigerator, for a period of time to enable the liquid substance to become frozen and hardened.

Prior to receiving an injection of the cytotoxic drug, the user will don the cap structure for a period of about 20 minutes, at which point the cytotoxic drug is injected into the individual. This individual receiving the cytotoxic drug will then wear the cap structure for about an additional twenty minutes. The head cap structure is effective in reducing the temperature and hence arterial blood flow around the scalp portion which thereby reduces the possibility of alopecia.

In a preferred aspect of the invention, the user first has a tourniquet applied around the scalp and the underside of the chin. This tourniquet is effective in reducing the major arterial flow whereas the cap structure is effective in reducing the smaller arterial flow along with capillary blood flow. One form of tourniquet is more fully illustrated in FIG. 10 of the drawings. In this case, the tourniquet 110 is comprised of a belt 112 having a buckle 114 at one end. In addition, the belt 112 is provided with graduations preferably raised embossed elements 116 with numerical indicia thereon. In this way, the physician or the aide of the physician can easily determine the proper size of the tourniquet for a particular individual, based on previous use with this same individual.

Thus, there has been illustrated and described a unique and novel cap structure having a freezable liquid substance therein for retaining a low temperature environment around a scalp portion of a user as well as a novel method of reducing alopecia. Thus, the present invention fulfills all of the objects and advantages sought therefore. It should be understood that many changes, modifications, variations, and other uses and applications will become apparent to those skilled in the art after considering this specification and the accompanying drawings. Therefore, any and all such changes, modifications, variations, and other uses which do not depart from the spirit and scope of the invention are deemed to be covered by the invention which is limited only by the following claims.

Having thus described my invention, what I desire to claim and secure by Letters Patent is:

1. A cap structure for reducing alopecia of a patient undergoing cytotoxic drug treatment by application of said structure to the head of said patient to create a cold environment around a substantial portion of the scalp of the patient, said structure comprising
   (a) a plurality of fabric panels comprised of a top panel, a back panel and two side panels connected by flexible members, each of said panels having at least one individual substance receiving chamber and a flexible fabric member with fasteners for operatively connecting each of said panels to at least one other panel in order to faciliate conforming said panels into said cap structure to fit closely around the scalp portion of the patient, and (b) a substance in each of the internal chambers in each of said fabric panels capable of being reduced to a low temperature substantially below body temperature and retaining said low temperature for a substantial period thereby to maintain a reduced temperature environment about the scalp portion of the patient for a period before and after said treatment.

* * * * *